US00PP22811P2

(12) United States Plant Patent
Kordes

(10) Patent No.: US PP22,811 P2
(45) Date of Patent: Jun. 26, 2012

(54) MINIATURE ROSE PLANT NAMED 'KORPOT022'

(50) Latin Name: *Rosa hybrida*
Varietal Denomination: KORpot022

(75) Inventor: Tim-Hermann Kordes, Klein Offenseth-Sparrieshoop (DE)

(73) Assignee: W. Kordees' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/066,499

(22) Filed: Apr. 14, 2011

(51) Int. Cl.
*A01H 5/00* (2006.01)

(52) U.S. Cl. ..... Plt./116

(58) Field of Classification Search ..... Plt./116, Plt./121, 123, 128
See application file for complete search history.

*Primary Examiner* — Kent L Bell

(57) ABSTRACT

A new and distinct variety of rose with long lasting, novel lavender flowers, and attractive foliage with good disease resistance. It exhibits uniform, compact growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot022'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003 the crossing was between a non-patented 'un-named seedling' and a non-patented 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot022'.

SUMMARY OF THE INVENTION

The new rose plant may be distinguished from its seed parent, an 'un-named seedling', by the following combination of characteristics:

1. The growth habit of 'KORpot022' is more than the growth habit of the seed parent.
2. The mildew resistance of 'KORpot022' is good while the mildew resistance of the seed parent is only fair.

The new rose plant may be distinguished from its pollen parent, an 'un-named seedling' by the following combination of characteristics:

1. 'KORpot022' is more compact and less vigorous than the pollen parent.

2. The flower size of 'KORpot022' is small while the flower size of the pollen parent is medium.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpot022' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot022' was selected in May 2004 from the seedling beds to be asexually propagated for further evaluation. The first asexual propagation of 'KORpot022' was done by budding to seedling understocks in July 2004 at the inventor's nursery in Offenseth-Sparrieshoop, Germany.

This initial and other subsequent propagations conducted in controlled environments demonstrate that 'KORpot022' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, and leaves of 'KORpot022'.

DETAILED BOTANICAL DESCRIPTION

The following is a description of 'KORpot022', as observed growing in July 2010 in a nursery in Jackson County, Oreg. on plants four months of age. Color references are made using The Royal Horticultural Society (London, England) Colour Chart, 2001 except where common terms of color are used.

For a comparison, several physical characteristics of the rose variety 'KORflieder', a non patented rose variety from the same are compared to 'KORpot022' in Table 1.

TABLE 1

| Characteristic | 'KORpot022' | 'KORflieder' |
|---|---|---|
| Bud Form | Short, pointed ovoid. | Very long, and High Centered. |
| Petal Reflex | Slight. | Double reflex |
| Average leaf size. | 65 mm × 50 mm. | 70-80 mm × 40-55 mm. |

Parents:

*Seed parent*.—An 'un-named seedling'.

*Pollen parent*.—An 'un-named seedling'.

Classification:

*Botanical classification*.—*Rosa hybrida*, 'KORpot022'.

*Commercial classification*.—Miniature rose.

FLOWER AND FLOWER BUD

Blooming habit: Recurrent.

Flower bud:

*Size*.—Upon opening, 20-25 mm in length from base of receptacle to end of bud and 10-15 mm diameter at its widest point.

*Bud form*.—Short. Pointed ovoid.

*Bud color*.—As sepals first unfold, bud color is Purple Group 77C. When ¼ open, the upper surface of petals is Purple Group 76C and the lower surface is Purple Group 77D. The Guard petals have intonations of Green Group 146B.

*Sepals*.—Color: Upper surface Green Group 138A. Lower surface Green Group 146B. Size: Average 25 mm long×8 mm wide. Shape: Sepals generally subulate. Sepal apex is generally cirrose. Strong foliaceous appendages on three of the five sepals. Base is flat at union with receptacle. Quantity: Five. Margins: With stipitate glands. Surface texture: Inner side: Pubescent. Outer side: Smooth. Stipitate glands are present.

Receptacle:

*Surface*.—Smooth. Stipitate glands absent.

*Color*.—Yellow-Green Group 144B.

*Shape*.—Urn-shaped.

*Size*.—7 mm (h)×4 mm (w).

Peduncle:

*Surface*.—With fine hairs and stipitate glands.

*Length*.—20-25 mm average length.

*Diameter*.—1.5-2.5 mm average diameter.

*Color*.—Yellow-Green Group 144A.

*Strength*.—Strong.

*Borne*.—Multiple flower buds per stem, generally 1 to 4.

Flower bloom:

*Fragrance*.—None.

*Duration*.—On the plant 4-6 days.

*Size*.—Small flowered pot rose. When open, the average flower diameter is 45 mm and the average flower height is 25 mm.

*Form*.—Shape of flower when viewed from the side: Upon opening, upper part: Cupped. Upon opening, lower part: Flattened convex. Open flower, upper part: Flattened convex. Open flower, lower part: Flat.

Color:

*Upon opening, petals*.—Outermost petals: Outer Side: Middle and upper zone: Purple Group 76A. Basal zone: Transitions to Purple Group 76D. Inner Side: Middle and upper zone: Purple Group 76A. Basal zone: Transitions to Purple Group 76D. Innermost petals: Outer Side: Purple Group 76B. Inner Side: Middle and upper zone: Purple Group 76A. Basal zone: Transitions to Purple Group 76D.

*Upon opening, basal petal spots*.—Basal petal spot, outermost petals: Outer Side: Yellow Group 2D. Inner Side: White Group 155A. Basal petal spot, innermost petals: Outer Side: White Group 155A. Inner Side: White Group 155A.

*After opening, petals*.—Outermost petals: Outer Side: Purple Group 76C. Intonations of Violet Group 85D in the basal zone. Inner Side: Purple Group 76D. Intonations of Violet Group 85D in the basal zone. Innermost petals: Outer Side: Purple Group 76C. Intonations of Violet Group 85D in the basal zone. Inner Side: Purple Group 76D. Intonations of Violet Group 85D in the basal zone.

*After opening, basal petal spots*.—Basal petal spot, outermost petals: Outer Side: White Group 155A. Inner Side: White Group 155A. Basal petal spot, innermost petals: Outer Side: White Group 155A. Inner Side: White Group 155A.

General tonality: On open flower Purple Group 76B. No change in the general tonality at the end of the $6^{th}$ day. Afterwards, general tonality is Purple Group 77C.

Petals:

*Petal count*.—Approximately 30-35 petals under normal conditions.

*Petal reflex*.—Petals reflex slightly.

*Petal edge*.—With point in center of margin.

*Petal shape*.—Deltoid. Apex shape is pointed. Shape of base is deltoid.

*Petal size:* 19 mm long and 15 mm wide.

*Thickness*.—Average.

*Petal arrangement*.—Not formal.

Petaloids: Present.

*Petaloid count*.—Average of 4-7 per flower.

*Petaloid size*.—Petaloids are 9 mm long and 3 mm wide.

*Petaloid color*.—Color of inner side is Purple Group 76D. Color of outer side is Red-Purple Group N74C.

*Petaloid texture*.—Smooth.

*Margins*.—Entire, smooth.

*Petaloid shape*.—Apex: Acute. Base: Obtuse.

Reproductive organs:

*Pistils*.—Approximately 25 present. Stigmas: Location: Slightly superior in position to anthers. Color: Greyed-Yellow Group 160B. Styles: Length: 5 mm long. Color: Greyed-Yellow Group 160B.

*Stamens*.—Approximately 35 on average and regularly arranged. Anthers: Size: 2 mm long. Color: Greyed-Orange Group 163C. Pollen: Absent. Filaments: Color: Greyed-Yellow Group 160D. Length: 4 mm.

THE PLANT

*Plant growth*.—Slow. Compact. When grown as a 10 cm container plant the average plant height is 20 cm and the average plant width is 18 cm.

*Stems*.—Stem color: Young wood: Yellow-Green Group 144A. Older wood: Yellow-Green Group 144A. Stem surface: Young wood: Smooth. Older wood: Smooth.

*Prickles*.—Present. Incidence: 3-5 per 10 cm of stem. Size: Average length: 3 mm. Color: Immature prickles: Yellow Group 144D. Mature prickles: Yellow-Orange Group 22A. Senescing to Greyed Orange Group N167A. Shape: Linear. Anthocyanin: None observed.

*Leaves and leaflets*.—Normally 5 leaflets on normal leaves in middle of the stem. Venation pattern: Pyramidal net pattern. Leaf size: 65 mm (l)×50 mm (w). Quantity: Average. Texture: Thin. Upper side of leaflet: Semi glossy. Under side of leaflet: Matte and Rough. Color, mature foliage: Upper Leaf Surface: Green Group 139A. Lower Leaf Surface: Yello-Green Group 147B. Color, juvenile foliage: Upper Leaf Surface: Green Group 137B. Lower Leaf Surface: Green Group 138B. Anthocyanin intonation: Intonations of Greyish-Red Group 180B.

*Stipules*.—Size: 15 mm long. 2 mm between the distal tips of the stipule. Stipule color: Yellow-Green Group 144B. Shape: Apex: Pointed. Base: Flat. Presence of stipitate glands: Present. Margins: With stipitate glands.

*Petiole*.—Length: 15 mm. Diameter: 1-1.5 mm. Petiole color: Yellow-Green Group 144B. Underneath: Smooth. Stipitate glands: Lacking.

*Petiole rachis*.—Length: 35 mm. Diameter: 1.25 mm. Color: Yellow-Green Group 144B. Underneath: Primarily smooth. Margins: Entire. Prickles: Present on underside. 1-2 prickles per leaf. Stipitate glands: Lacking.

*Leaflets*.—Size: Average size of the terminal leaflet is 35 mm (l)×25 mm (w). Shape: Base: Ovate. Apex: Acute. Margins: Finely serrated. Texture: Thin.

Hips/seed formation: None observed.

Winter hardiness: To date, the variety has been grown successfully in Zone 5.

Disease resistance: Moderate resistance to Powdery mildew (*Sphaerotheca pannosa*),and *Botrytis* (*Botrytis cinerea*) diseases under normal growing conditions.

I claim:

1. A new and distinct variety of rose plant, as described and illustrated herein.

* * * * *

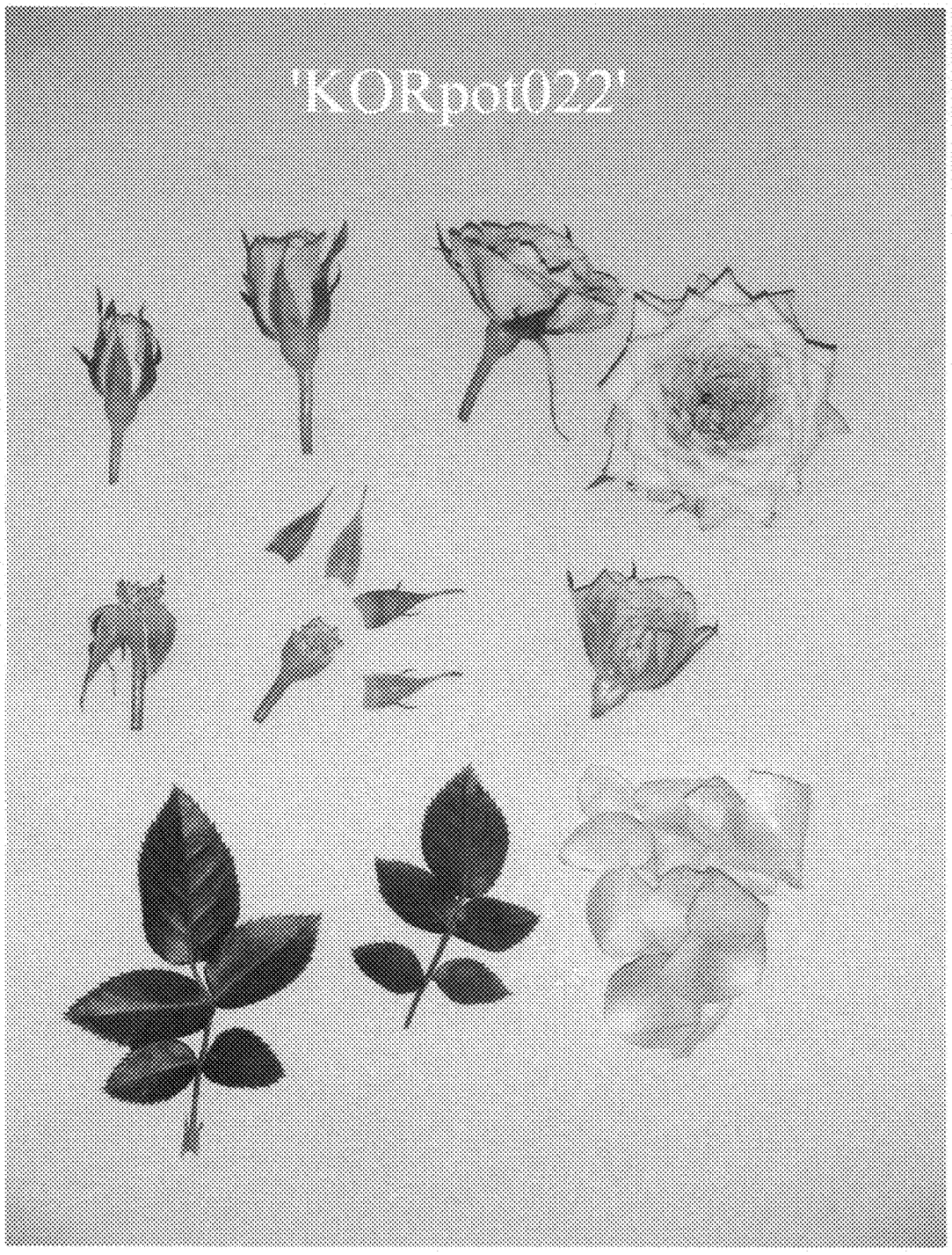
'KORpot022'